United States Patent
Yoshioka et al.

(10) Patent No.: US 11,385,195 B2
(45) Date of Patent: Jul. 12, 2022

(54) GAS DETECTOR AND GAS DETECTION METHOD

(71) Applicant: Figaro Engineering Inc., Minoo (JP)

(72) Inventors: Kenichi Yoshioka, Minoo (JP); Akiko Omori, Minoo (JP)

(73) Assignee: Figaro Engineering Inc., Osaka (JP)

( * ) Notice: Subject to any disclaimer, the term of this patent is extended or adjusted under 35 U.S.C. 154(b) by 665 days.

(21) Appl. No.: 16/469,356

(22) PCT Filed: Dec. 28, 2017

(86) PCT No.: PCT/JP2017/047221
§ 371 (c)(1),
(2) Date: Jun. 13, 2019

(87) PCT Pub. No.: WO2018/131503
PCT Pub. Date: Jul. 19, 2018

(65) Prior Publication Data
US 2019/0302046 A1    Oct. 3, 2019

(30) Foreign Application Priority Data
Jan. 12, 2017 (JP) .............................. JP2017-003304

(51) Int. Cl.
*G01N 27/12* (2006.01)
*B81B 7/00* (2006.01)
*G01N 27/18* (2006.01)
*G01N 33/00* (2006.01)

(52) U.S. Cl.
CPC ......... *G01N 27/124* (2013.01); *B81B 7/0087* (2013.01); *B81B 7/0096* (2013.01); *G01N 27/12* (2013.01); *G01N 27/128* (2013.01); *G01N 27/18* (2013.01); *G01N 33/0013* (2013.01)

(58) Field of Classification Search
CPC .. G01N 27/124; G01N 27/128; B81B 7/0087; B81B 7/0096
See application file for complete search history.

(56) References Cited

U.S. PATENT DOCUMENTS

| 9,182,366 B2 | 11/2015 | Izawa et al. | |
| 2014/0212979 A1* | 7/2014 | Burgi | G01N 27/124 422/83 |
| 2014/0223995 A1 | 8/2014 | Buhler et al. | |
| 2015/0201065 A1* | 7/2015 | Shim | H04W 88/02 455/556.1 |

FOREIGN PATENT DOCUMENTS

| JP | 2000341375 A5 | 12/2000 |
| JP | 200958389 A | 3/2009 |
| JP | 2012172973 A | 9/2012 |
| JP | 5748211 B2 | 12/2012 |

* cited by examiner

*Primary Examiner* — Paul M. West
(74) *Attorney, Agent, or Firm* — The Webb Law Firm

(57) ABSTRACT

A gas sensor and the drive circuit for the sensor are installed within a mobile electronic device. The gas sensor is intermittently heated to an operating temperature for detecting gases and kept at an ambient temperature for other periods. When a sensor of the mobile electronic device detects that the device is placed in a closed space, the heating of the metal oxide semiconductor is halted. When the sensor detects that the mobile electronic device has been taken out from the closed space, the heating of the metal oxide semiconductor is resumed. The poisoning of the gas sensor by siloxanes or the like is prevented.

9 Claims, 6 Drawing Sheets

F I G. 2
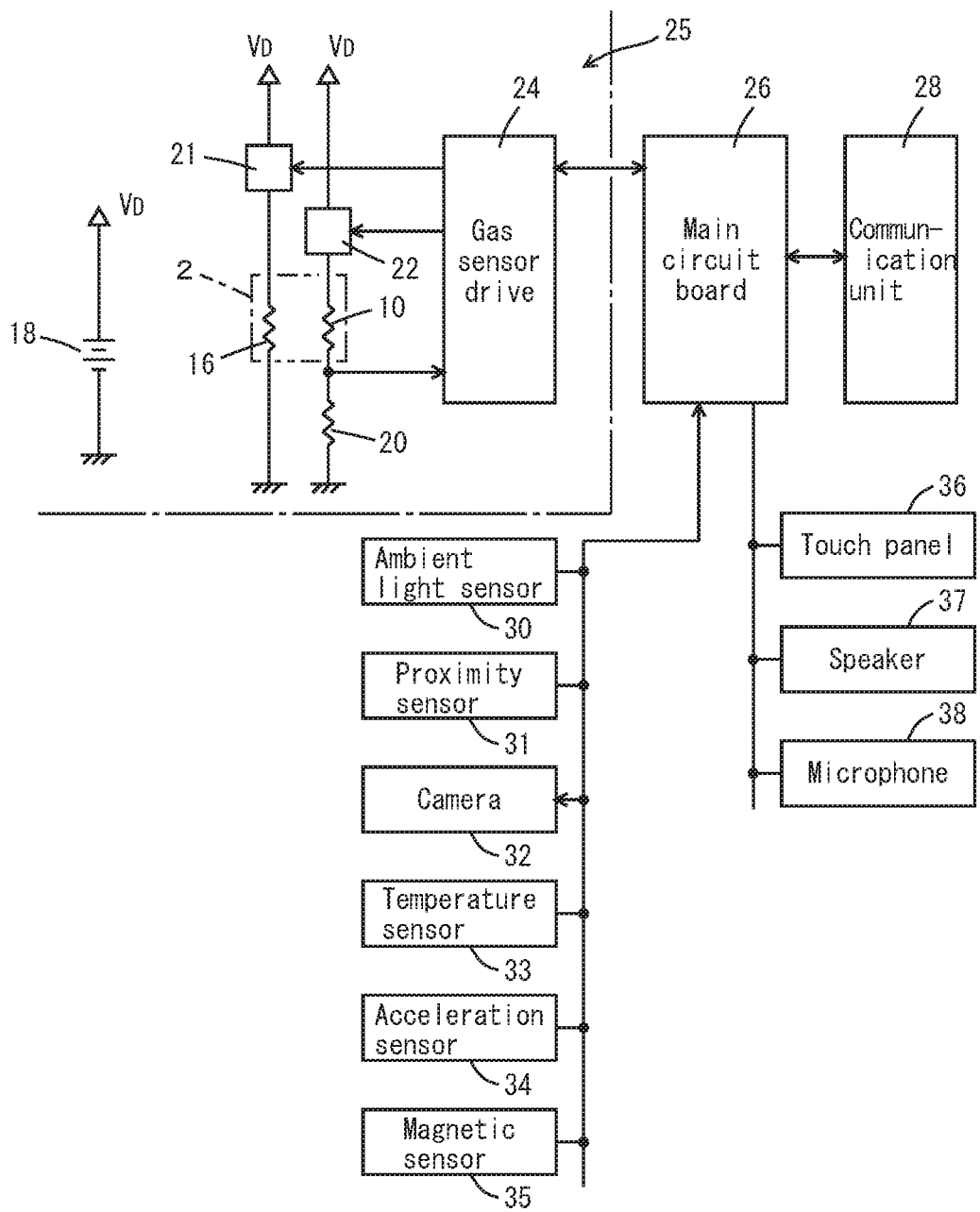

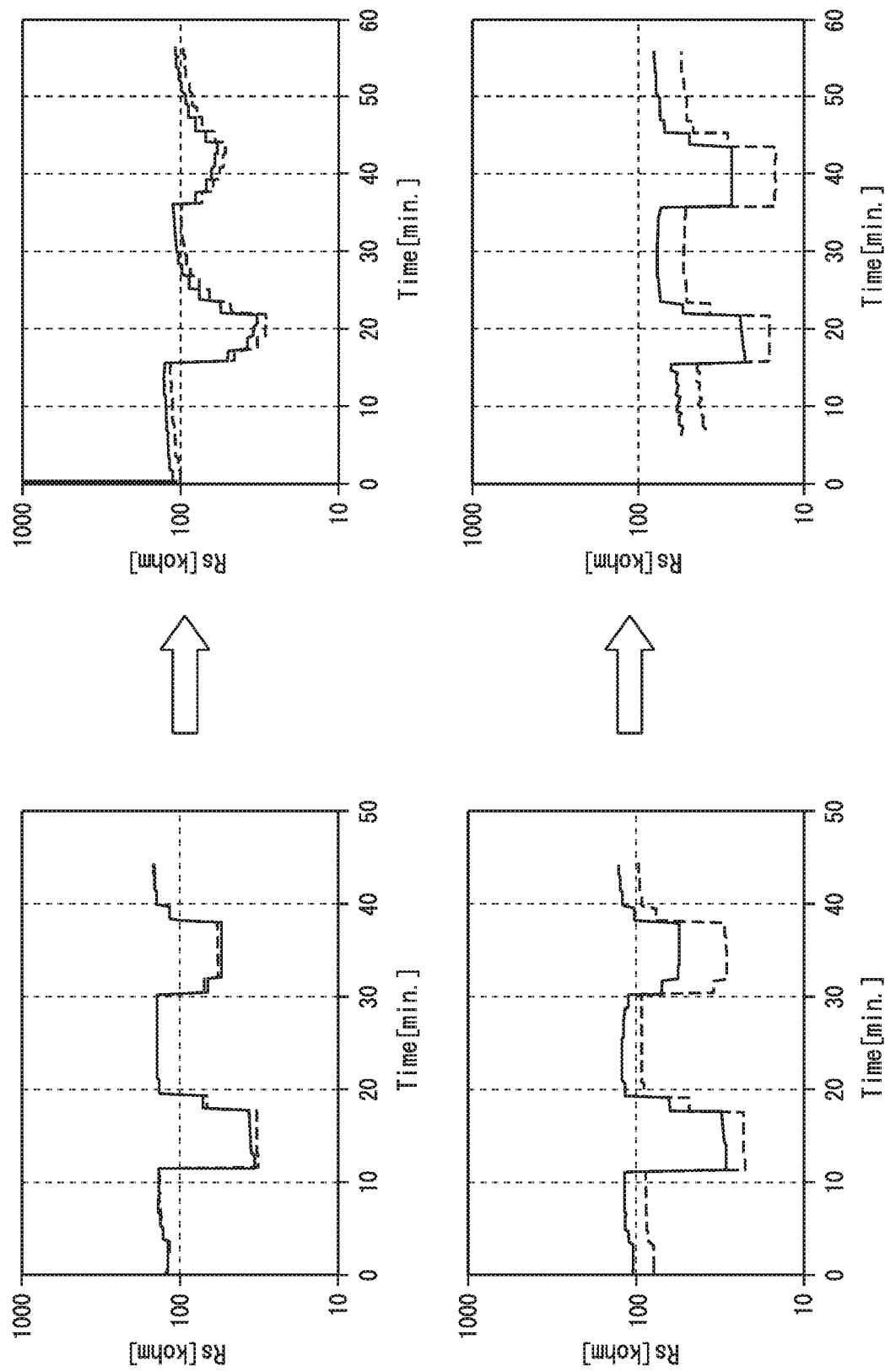

GAS DETECTOR AND GAS DETECTION METHOD

CROSS-REFERENCE TO RELATED APPLICATIONS

This application is the United States national phase of International Application No. PCT/JP2017/047221 filed Dec. 28, 2017, and claims priority to Japanese Patent Application No. 2017-003304 filed Jan. 12, 2017, the disclosures of which are hereby incorporated by reference in their entirety.

BACKGROUND OF THE INVENTION

Field of the Invention

The present invention relates to a gas detector and a gas detection method.

Description of Related Art

The present inventors and others have proposed a method for preventing the contamination of MEMS gas sensors (Patent Document 1: JP5748211B). According to the method, a MEMS gas sensor is operated with a 30 seconds period and is heated to 100° C. for 0.4 second in order to remove contaminants such as ethanol and siloxanes. Then, the gas sensor is heated about 500° C. for detecting methane.

PRIOR ART DOCUMENT

Patent Document

Patent Document 1: JP5748211B

SUMMARY OF THE INVENTION

Problem to be Solved

When gas sensors are installed within mobile electronic devices such as smartphones, gas sensors are sometimes confined in brief cases, handbags, drawers, and so on. They are closed spaces and have poor ventilation. Further, siloxane gases are generated from silicone rubbers used in the covers of the mobile electronic devices; they are also generated from silicone compounds contained in cosmetics within the handbags or drawers, and form other small items. MEMS gas sensors are contaminated by the siloxane gases in these closed spaces, and as a result, the response of the gas sensors to gases decreases in both the magnitude and the speed.

The object of the invention is to prevent the contamination of MEMS gas sensors installed within mobile electronic devices.

Means for Solving the Problem

The gas detector according to the invention comprises a MEMS gas sensor having a film-like metal oxide semiconductor having an electrical resistance varying according to gases and a heater; and a drive circuit supplying electric power to the heater intermittently to heat the metal oxide semiconductor to an operating temperature and sampling the electrical resistance of the metal oxide semiconductor at the operating temperature.

The gas detector is configured to be installed within a mobile electronic device. The drive circuit halts the heating of the metal oxide semiconductor to the operating temperature when a sensor of the mobile electronic device detects the mobile electronic device is placed in a closed space and then resumes the heating of the metal oxide semiconductor to the operating temperature when the sensor of the mobile electronic device detects the mobile electronic device has been taken out from the closed space.

The gas detection method according to the invention uses a MEMS gas sensor having a film-like metal oxide semiconductor having an electrical resistance varying according to gases, and a heater, and supplies electric power to the heater intermittently to heat the metal oxide semiconductor to an operating temperature by a drive circuit, and samples the electrical resistance of the metal oxide semiconductor at the operating temperature by the drive circuit. Further, the gas detector is installed within a mobile electronic device.

The gas detection method according to the invention comprises:

halting by the drive circuit the heating of the metal oxide semiconductor to the operating temperature when a sensor of the mobile electronic device detects the mobile electronic device is placed in a closed space; and resuming by the drive circuit the heating of the metal oxide semiconductor to the operating temperature when the sensor of the mobile electronic device detects the mobile electronic device has been taken out from the closed space.

As shown in FIG. 9, when in contact with poisoning gases such as silicone gases, the operation of MEMS gas sensors is halted; in other words, the heating of the metal oxide semiconductor of the gas sensors to the operating temperature is halted. Then, the contamination of the MEMS gas sensors is prevented. When the mobile electronic devices are contained in closed spaces where ventilation is insufficient, the contaminant gas concentrations increase, and therefore, the contamination arises. Here, the fact that the mobile electronic devices are in closed spaces is detectable by sensors in the mobile electronic devices. In addition, MEMS gas sensors are more easily contaminated than conventional gas sensors, since the heating periods of MEMS gas sensors are made shorter for reducing their power consumptions.

Preferably, the sensor of the mobile electronic device is an ambient light sensor or a proximity sensor. These sensors are installed in many of the mobile electronic devices. The ambient light sensor may detect that the surroundings are dark and therefore that the device is placed in a closed space. The proximity sensor may detect that the inner sides of briefcases, handbags, drawers, or the like and therefore that the device is placed in a closed space.

Preferably, the drive circuit is configured and programmed to heat the metal oxide semiconductor to the operating temperature with a predetermined period and to halt the heating of the metal oxide semiconductor to the operating temperature when the sensor of the mobile electronic device detects the mobile electronic device is placed in a closed space over a plurality of the periods. The contamination is caused when the gas sensor is placed in a closed space over a time duration longer than the operational period of the gas sensor. Therefore, when the heating is halted upon the detection that the device is placed in a closed space over plural periods, the contamination is prevented and the operation of the gas sensor is not unnecessary halted.

Preferably, the drive circuit is configured and programmed to carry out a heat-cleaning of the metal oxide semiconductor when resuming the heating of the metal oxide semiconductor to the operating temperature. Here, the heat-cleaning means additional heating of the metal oxide semiconductor which is not carried out at normal operation. The heat-cleaning eliminates the contaminant gases and also other gases both adsorbed when the heating was halted. Therefore, the reliability of gas sensor signals when the operation is resumed is enhanced.

Preferably, the drive circuit is configured and programmed to count up the duration of halting the heating of the metal oxide semiconductor and adjust the condition of the heat-cleaning according to the counted duration. Thus, heat-cleaning dependent upon the duration of the halting is carried out. For example, no heat-cleaning may be performed for a short halting of the operation and the heat-cleaning duration is made longer when the operation has been halted for a longer duration.

BRIEF DESCRIPTION OF THE DRAWINGS

FIG. 9 A characteristic diagram indicating the influence of contamination to gas sensors: the upper diagram indicates those in a conventional example and the lower diagram indicates those in the embodiment.

DESCRIPTION OF THE INVENTION

The best embodiment for carrying out the invention will be described in the following Embodiment.

Figure 1:
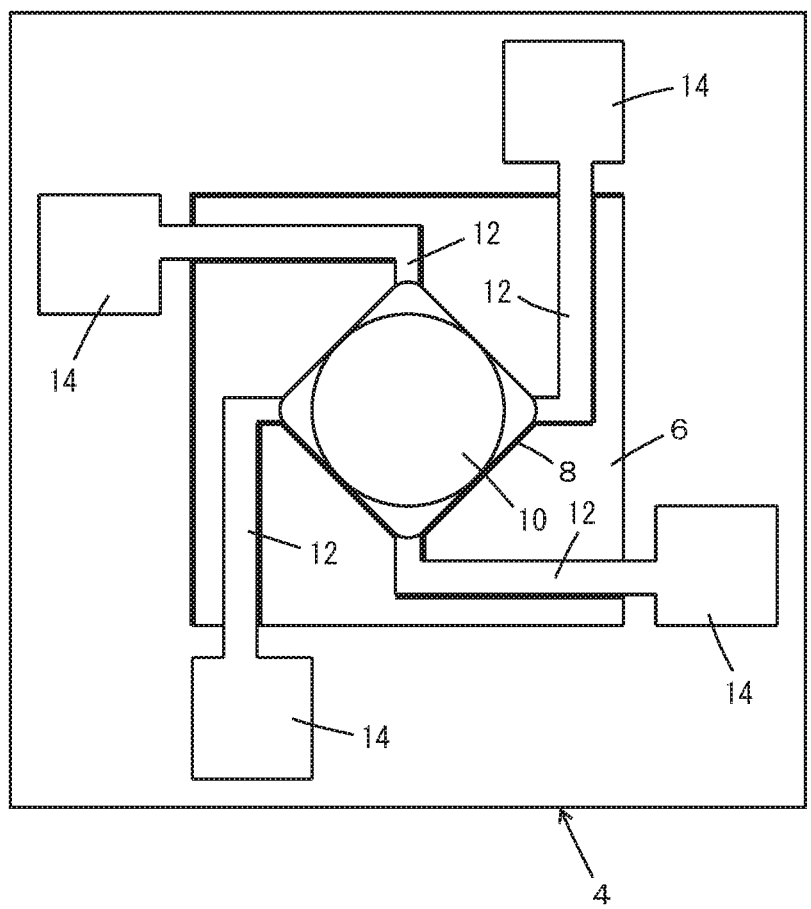
FIG. 1 A plan view of the major portion of the MEMS gas sensor used in the embodiment FIG. 2 A block diagram of the gas detector according to the embodiment FIG. 3 A waveform diagram of the heater power to the gas sensor when driven FIG. 4 A flowchart indicating the drive algorithm of the gas sensor according to the embodiment FIG. 5 A waveform diagram of the heater power to the gas sensor according to the embodiment when returned from a closed space FIG. 6 A waveform diagram of the heater power to the gas sensor according to a modification when returned from a closed space FIG. 7 A waveform diagram of the heater power to the gas sensor according to a second modification when returned from a closed space FIG. 8 A waveform diagram of the heater power to the gas sensor according to a third modification when returned from a closed space: the upper diagram indicates the normal heating pattern, the middle diagram indicates a heating pattern in a closed space, and the lower diagram indicates the normal heating pattern when returning from a closed space.

FIGS. 1 to 9 show the embodiment and the characteristics. FIG. 1 shows an example of MEMS gas sensors 2. It has a substrate 4 such as silicon and suitable for micro machining, and the substrate 4 has a cavity 6 that penetrates the substrate 4 and a support film 8 over the cavity 6 supported by, for example, four beams 12. On the support film 8, a film-like heater (not shown) and film-like electrodes (not shown) are formed, and a metal oxide semiconductor film 10 covers them. The metal oxide semiconductor film 10 is, for example, a thick film of SnO2 and may be other metal oxide semiconductor films such as In2O3, WO3, and so on. In addition, the metal oxide semiconductor film 10 may be a thin film. Further, both ends of the heater and ends of the electrodes are connected via the beams 12 to the pads 14.

The structures and materials for the gas sensor 2 are arbitrary, and for example, the support film 8 may be a diaphragm covering the cavity 6. In addition, the heater and the electrodes may be provided on the same layer, or alternatively, the heater may be covered by an insulating film and the electrodes may be provided on the insulating film. Further, without the electrodes, the parallel electrical resistance value of the metal oxide semiconductor and the heater may be detected. A catalytic layer may be provided over the metal oxide semiconductor film for eliminating unnecessary gases. A separate and independent filter from the substrate 4 may be provided in order for unnecessary gases to be adsorbed by the filter.

FIG. 2 shows the gas sensor 2, a drive circuit 25 for the gas sensor, the main circuit board 26 of the mobile electronic device, and so on. Indicated by 16 is the heater of the gas sensor 2, by 18 the power supply such as a battery, by 20 the load resistor, and by 21,22 switches. A gas sensor drive 24 makes the switch 21 on and off in order to drive the heater 16, makes the switch 22 on and off, and measures the voltage over the load resistor 20 via an AD converter not shown. The voltage is determined by the electrical resistance of the metal oxide semiconductor 10. Gases are detected according to the voltage over the load resistor 20, relevant signal processing may be performed by the gas sensor drive 24 or by the main circuit board 26.

The main circuit board 26 is the major portion of the mobile electronic device and communicates with the outside world through a communication unit 28. Further, the mobile electronic device is provided with an ambient light sensor 30 for detecting the ambient brightness, a proximity sensor 31 for detecting proximate objects such as a human body, a camera 32, a temperature sensor 32, an acceleration sensor 34, a magnetic sensor 35 for detecting terrestrial magnetism, and so on. Further, a touch panel 36, a speaker 37, a microphone 38, and so on are provided within the mobile electronic device. The gas sensor drive 24 needs the signal from the ambient light sensor 30 or the proximity sensor 31. While FIG. 2 indicates such that the gas sensor drive receives these signals from the main circuit board 26, it may directly receive the signal of the ambient light sensor 30 or the proximity sensor 31 via a bus (not shown). Here, the drive circuit 25 indicates a circuit in the upper left portion in FIG. 2 except for the gas sensor 2 enclosed by a chain line. The power supply 18 is a common power supply for the entire mobile electronic device. In addition, the drive circuit 25 has a structure adapted for the connection with the main circuit board 26.

Figure 3:
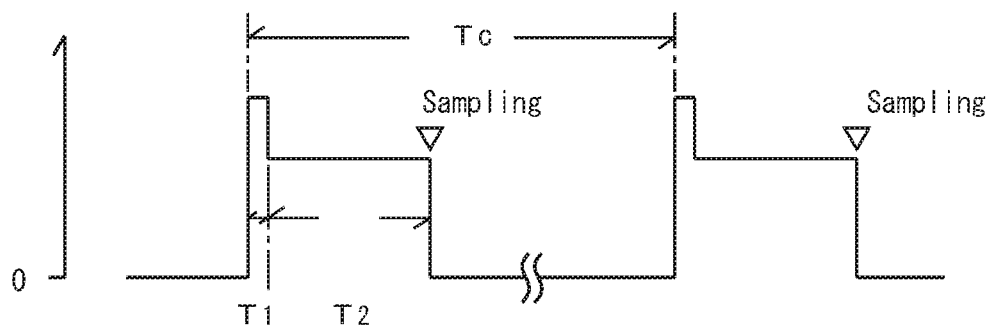

FIG. 3 indicates the heater power or the heater voltage to the gas sensor 2 during the normal operation. The gas sensor 2 has an operation period Tc such as 10 seconds to 10 minutes. For a time period T1 such as 0.1 second to 1 second, it is heated to a higher temperature (for example, 400 to 500° C.) than the operating temperature (for example, 300 to 400° C.), and then heated to the operating temperature for a time period T2 such as 1 second to 10 second. For example, at the end of the period T2, the voltage over the load resistor is sampled, and the gas sensor drive 24 or the main circuit board 26 detects gases. During the remaining time duration other than T1 and T2, the gas sensor 2 is kept at ambient temperatures. In addition, when gases are detected, the operation period Tc may be shortened. The high-temperature heating during the period T1 may be omitted, and the temperature may be changed only between the ambient temperatures and the operating temperature. Further, the timing for sampling the voltage over the load resistor is arbitrary.

Figure 4:
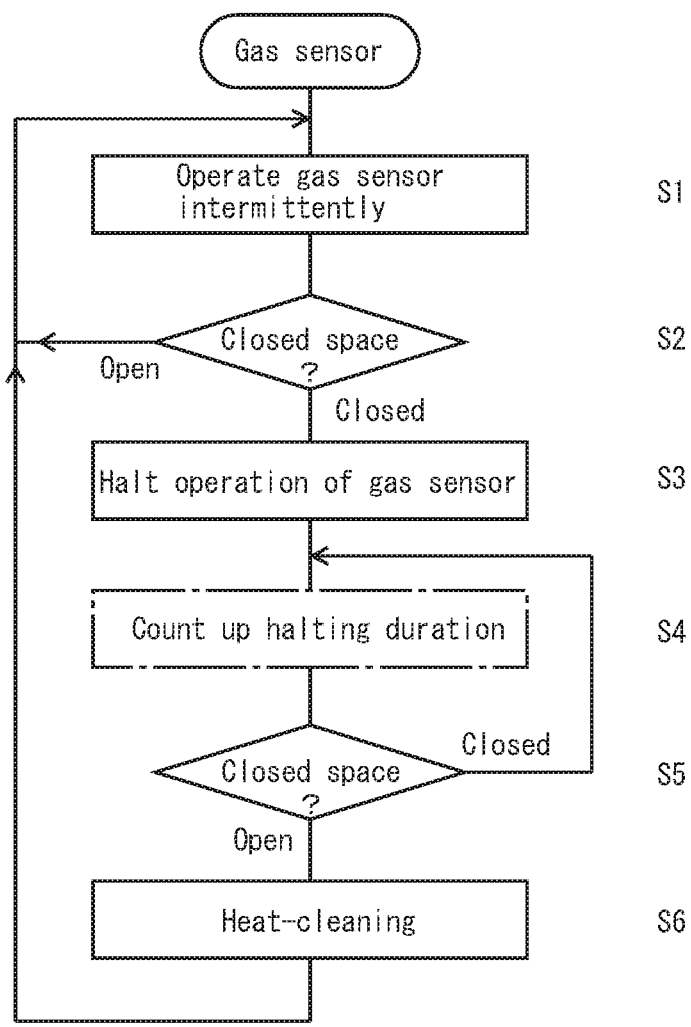

FIG. 4 indicates the algorithm for halting the operation of the heater when detecting the gas sensor 2, and therefore, the mobile electronic device are placed in a closed space. The gas sensor 2 is driven with the period Tc, and for example, the detection whether the mobile electronic device is placed in a closed space is performed for every period (step 1). Here, a closed space means an enclosed space such as those within briefcases, handbags, pockets, drawers, and so on. The detection period of the closed space may be longer than the operation period Tc of the gas sensor 2.

The ambient light sensor 30 may detect that the surrounding is dark and therefore, may detect that the mobile electronic device is placed in a closed space. When the proximity sensor 31 detects an object always, this is a peculiar phenomenon to a closed space. Moreover, the camera 32 may detect the brightness of the surroundings. While the type of sensors for detecting a closed space is arbitrary, a sensor installed within a mobile electronic device is used; a preferable sensor is the ambient light sensor 30 and the proximity sensor 31. As a remark, the ambient light sensor 30 may not distinguish a night time and a closed space. However, it is detectable, according to inputs to the touch panel 36 or the microphone 38, that the mobile electronic device is in operation by a user; when in use the device may be estimated not in a closed space.

While not directly related to the prevention of the contamination of the gas sensor 2, the acceleration sensor 34 and the magnetic sensor 35 may detect that the mobile electronic device is placed in the same position for a long duration without being carried, and in this instance, the operation of the gas sensor 2 may be halted. In many cases, this means the owner of the device is in bed, and the detection of air quality in the bedroom is not important. The ambient light sensor 30 makes the operation of the gas sensor 2 halted when the owner is in bed. However, the proximity sensor 31 makes the operation of the gas sensor 2 continue when the owner is in bed.

The target of the detection is that the gas sensor 2 is placed in a closed space for a duration longer than one operation period Tc. For example, the detection of whether the device is placed in a closed space is performed plural times for one operation period Tc, and when all of the detections indicate a closed space, the gas sensor 2 (the mobile electronic device) is considered to be placed in a closed space. Alternatively, when it is detected over plural operation periods that the device has been in a closed space, the gas sensor is considered to be kept in a closed space (step 2).

When it is detected that the device is placed in a closed space, the operation of the gas sensor 2 is halted (step 3). Since the heater of the gas sensor 2 is not operated, the silicone gas adsorbed in the metal oxide semiconductor is prohibited from changing to compounds that are hardly to desorb by polymerization or the like. Further, a local convectional flow around the metal oxide semiconductor is prevented to occur, and therefore, the adsorption of silicone gases to the metal oxide semiconductor is reduced. In addition, as taught in the patent document 1, organic solvents such as ethanol may contaminate MEMS gas sensors, and therefore, the contaminants are not limited to silicone gases.

When halting the operation of the gas sensor, the duration when the operation is halted, for example, the number of the operation periods Tc, is counted up (step 4). However, the halting duration may not be counted.

Within a closed space, the detection whether the device is placed in a closed space is performed for every operation period Tc, and when it is detected that the device has been taken out from a closed space (step 5), a heat-cleaning is performed in order to recover the gas response performance (step 6). Heating to 400 to 500° C. for 30 seconds to 10 minutes is estimated enough long for making the adsorbed silicone gases desorb, even if some of them are polymerized. However, without the heat-cleaning, the gas sensor may be returned to normal operation shown in FIG. 3 upon the detection of open space.

Figure 5:
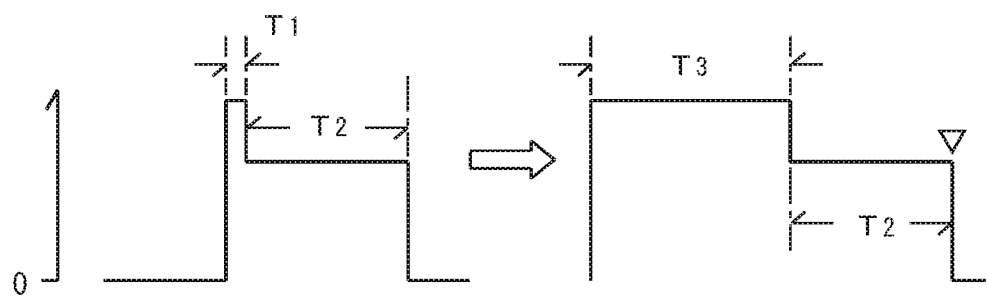
Figure 6:
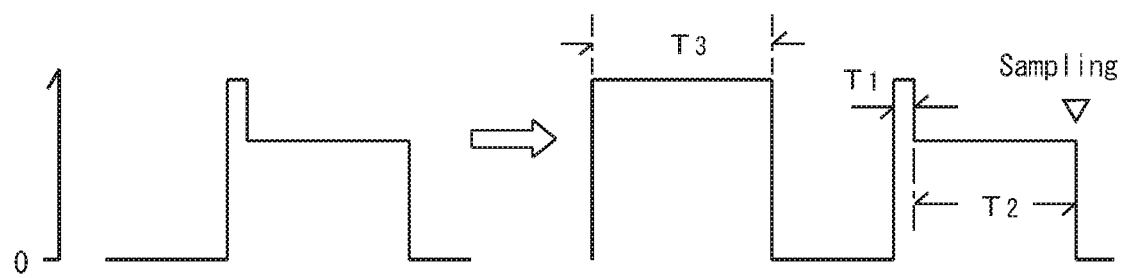
Figure 7:
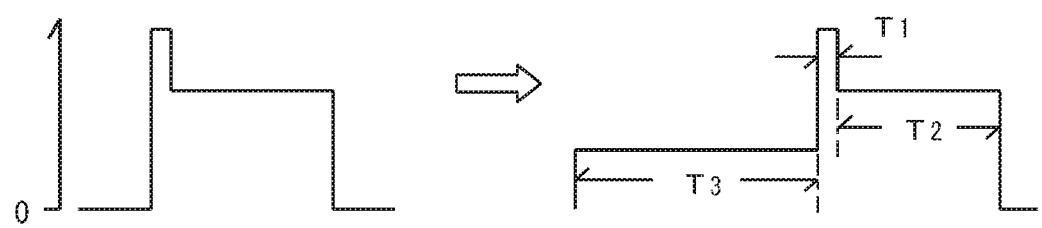

FIGS. 5 to 7 indicate examples of the heat-cleaning, where the left column indicates the normal operation pattern, and where the right column indicates the operation patterns with the heat-cleaning. In FIG. 5, the period for heating to the temperature higher than the operating temperature is extended from the normal period T1 to a heat-cleaning duration T3 of 30 seconds to 10 minutes. Thus, contaminant gases and various gases both adsorbed when the operation of the gas sensor 2 was halted are removed.

In FIG. 5, after the heat-cleaning, the metal oxide semiconductor is immediately heated to the operating temperature. However, as shown in FIG. 6, after the heat-cleaning for the period T3, the gas sensor 2 may be cooled to the ambient temperature and then it may be operated.

As shown in FIG. 7, the metal oxide semiconductor may experience a heat-cleaning at 80 to 200° C. for a period T3, and various gases adsorbed when the operation of the gas sensor 2 was halted are vaporized.

The heat-cleaning duration T3 is preferably determined, for example, according to the duration when the gas sensor 2 was placed in a closed space. For example, when the duration is relatively short (for example, from 10 minutes to 1 hour), heat-cleaning may be omitted, and when the duration is longer, the heat-cleaning period is preferably made longer.

Figure 8:
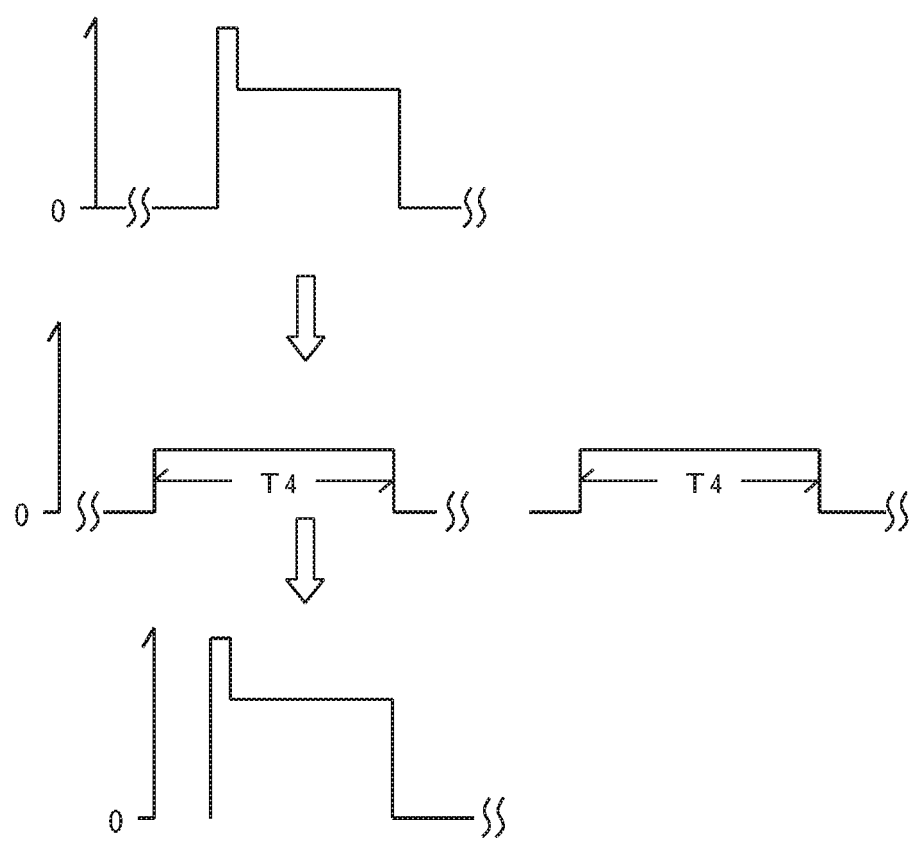

As shown in FIG. 9, when in contact with contaminant gases, the operation of the gas sensors 2 is halted; namely, the heater power is not added, and then the contamination is prevented. The heat-cleaning aims to remove various gases adsorbed when the operation of the gas sensors was halted. Therefore, the heat-cleaning may not be carried out. In addition, within a closed space, silicone or the like gases may be vaporized from the metal oxide semiconductor. FIG. 8 shows an example; when the gas sensor is placed in a closed space, the metal oxide semiconductor is heated to 80 to 200° C. or a similar temperature for a period T4 with a predetermined interval, and as a result, the adsorbed silicone gases and so on are vaporized. The upper stage in the drawing indicates the normal operation pattern, the middle stage indicates the operation pattern in a closed space, and as shown in the lower stage, the operation pattern is returned to the normal pattern when the gas sensor is taken out from a closed space.

FIG. 9 indicates the difference in contamination between a case where the gas sensors 2 were operated in an environment including a silicone gas (the upper row) and a case where the operation of the gas sensors was halted in the environment including a silicone gas (the lower row). The gas sensors were placed in an atmosphere including 1 ppm of a siloxane gas (D5) for 24 hours; the siloxane concentration was higher than those in handbags or the like. The gas responses of the gas sensors before the siloxane contact are shown in the left column of FIG. 9, and those after the siloxane contact are shown in the right column of FIG. 9. First, gas responses to 3 ppm H2 were measured and then, gas responses to 10 ppm ethanol were measured. The operation pattern of the gas sensors was already indicated in FIG. 3. The operation period Tc was 90 seconds, the period T1 was 1 second (the maximum temperature of the metal oxide semiconductor was about 400° C.), the period T2 (the operation temperature of the metal oxide semiconductor was about 300° C.) was 4 seconds. The metal oxide semiconductor was a thick film of SnO2 (the film thickness was about 20 micrometers).

The upper row of FIG. 9 shows the result when the gas sensors were continued to operate in the silicone atmosphere and the lower row shows the result when the gas sensors were halted in the silicone atmosphere. When the gas sensors were operated intermittently in the siloxane atmosphere, the gas response characteristic was decreased in both the magnitude of the response and the speed of the response. On the contrary, when the gas sensors were halted to operate in the silicone atmosphere, the magnitude of the gas response was maintained at almost the same value and the speed of the response was maintained. Thus, when, in the presence of a contaminant gas, the operation of the gas sensors is halted, the contamination of the gas sensors is prevented.

In addition, organic solvents such as ethanol cause contamination due to their polymerization in the metal oxide semiconductor (see the patent document 1), and the thermal energy necessary for the polymerization is supplied by heating the metal oxide semiconductor to the operating temperature. Therefore, with respect to organic solvent contaminants, the contamination of gas sensors is prevented by halting the gas sensor operation when in contact with them.

| Description of Reference Symbols | |
|---|---|
| 2 | MEMS gas sensor |
| 4 | Substrate |
| 6 | Cavity |
| 8 | Support film |
| 10 | Metal oxide semiconductor film |
| 12 | Beam |
| 14 | Pad |
| 16 | Heater |
| 18 | Battery |
| 20 | Load resistor |
| 21, 22 | Switch |
| 24 | Gas sensor drive |
| 25 | Drive Circuit |
| 26 | Main Circuit board |
| 28 | Communication unit |
| 30 | Ambient light sensor |
| 31 | Proximity sensor |
| 32 | Camera |
| 33 | Temperature sensor |
| 34 | Acceleration sensor |
| 35 | Magnetic sensor |
| 36 | Touch panel |
| 37 | Speaker |
| 38 | Microphone |

What is claimed is:

1. A gas detector comprising a MEMS gas sensor having a film-like metal oxide semiconductor having an electrical resistance varying according to gases and a heater; and
   a drive circuit supplying electric power to said heater intermittently to heat said metal oxide semiconductor to an operating temperature and sampling the electrical resistance of the metal oxide semiconductor at the operating temperature,
   wherein said gas detector is configured to be installed within a mobile electronic device,
   and wherein said drive circuit is configured and programmed to halt the heating of said metal oxide semiconductor to the operating temperature when a sensor of said mobile electronic device detects said mobile electronic device is placed in a closed space and to resume the heating of said metal oxide semiconductor to the operating temperature when the sensor of said mobile electronic device detects said mobile electronic device has been taken out from the closed space.

2. The gas detector according to claim 1, wherein said sensor of the mobile electronic device is an ambient light sensor or a proximity sensor.

3. The gas detector according to claim 2, wherein said drive circuit is configured and programmed to heat the metal oxide semiconductor to the operating temperature with a predetermined period and to halt the heating of said metal oxide semiconductor to the operating temperature when said sensor of said mobile electronic device detects said mobile electronic device is placed in a closed space over a plurality of the periods.

4. The gas detector according to claim 2, wherein said drive circuit is configured and programmed to carry out a heat-cleaning of said metal oxide semiconductor when resuming the heating of said metal oxide semiconductor to the operating temperature.

5. The gas detector according to claim 1, wherein said drive circuit is configured and programmed to heat the metal oxide semiconductor to the operating temperature with a predetermined period and to halt the heating of said metal oxide semiconductor to the operating temperature when said sensor of said mobile electronic device detects said mobile electronic device is placed in a closed space over a plurality of the periods.

6. The gas detector according to claim 5, wherein said drive circuit is configured and programmed to carry out a heat-cleaning of said metal oxide semiconductor when resuming the heating of said metal oxide semiconductor to the operating temperature.

7. The gas detector according to claim 1, wherein said drive circuit is configured and programmed to carry out a heat-cleaning of said metal oxide semiconductor when resuming the heating of said metal oxide semiconductor to the operating temperature.

8. The gas detector according to claim 7, wherein said drive circuit is configured and programmed to count up a duration when the heating of said metal oxide semiconductor is halted and to adjust a condition of the heat-cleaning according to the duration.

9. A gas detection method using a MEMS gas sensor having a film-like metal oxide semiconductor having an electrical resistance varying according to gases and a heater, and
   supplying electric power to said heater intermittently to heat said metal oxide semiconductor to an operating temperature by a drive circuit, and sampling the electrical resistance of the metal oxide semiconductor at the operating temperature by the drive circuit,
   wherein said gas sensor and said drive circuit are installed within a mobile electronic device,
   said method comprising:
   halting by said drive circuit the heating of said metal oxide semiconductor to the operating temperature when a sensor of said mobile electronic device detects said mobile electronic device is placed in a closed space; and
   resuming by said drive circuit the heating of said metal oxide semiconductor to the operating temperature when the sensor of said mobile electronic device detects said mobile electronic device has been taken out from the closed space.

\* \* \* \* \*